United States Patent [19]

Handelsman et al.

[11] Patent Number: 5,736,382
[45] Date of Patent: Apr. 7, 1998

[54] BACILLUS CEREUS STRAIN DGA34

[75] Inventors: Jo Handelsman; Lynn M. Jacobson; Eric V. Stabb, all of Madison, Wis.

[73] Assignee: Wisconsin Alumni Research Foundation, Madison, Wis.

[21] Appl. No.: 470,800

[22] Filed: Jun. 6, 1995

[51] Int. Cl.$^6$ .............................. C12N 1/20; C12P 13/00
[52] U.S. Cl. ..................... 435/252.5; 435/128; 435/158; 435/71.2
[58] Field of Search ........................... 435/252.5, 128, 435/158, 71.2

[56] References Cited

U.S. PATENT DOCUMENTS

| | | |
|---|---|---|
| 4,250,170 | 2/1981 | Kawaguchi et al. |
| 4,259,317 | 3/1981 | Vesely et al. |
| 4,877,738 | 10/1989 | Handelsman et al. |
| 5,049,379 | 9/1991 | Handelsman et al. |
| 5,543,301 | 8/1996 | Handelsman ........................ 435/252.1 |

FOREIGN PATENT DOCUMENTS

| | | |
|---|---|---|
| 0278 959 B1 | 8/1988 | European Pat. Off. |
| WO88/00966 | 2/1988 | WIPO. |

OTHER PUBLICATIONS

Bergey's Manual, "Part 15. Endospore–Forming Rods and Cocci," pp. 532–535 (1974).

Gurusiddaiah, S., et al., "Characterization of an Antibiotic Produced by a Strain of *Pseudomonas fluorescens* Inhibitory to *Gaeumannomyces graminis* var.*tritici* and *Pythium* spp.," *Antimicrob. Agents Chemother.*, 29:488–495 (1986).

Handelsman, J., et al., "Zoospore Lysis in Biocontrol of *Phytophthora megasperma* by *Bacillus cereus* UW85," Abstract, published Aug. 1987.

Handelsman, J., et al., "Biological Control of Damping–Off of Alfalfa Seedlings with *Bacillus cereus* UW85," *App. Environ. Microb.*, 56:713–718 (1990).

Handelsman, J., et al., "Microassay for Biological and Chemical Control of Infection of Tobacco by *Phytophthora parasitica* var. *nicotianae*," *Curr. Microb.*, 22:317–319 (1991).

Howell, C.R., and R.D. Stipanovic, "Control of *Rhizobium solani* on Cotton Seedlings with *Pseudomonas fluorescens* and With an Antibiotic Produced by the Bacterium," *Phytopathology*, 69:480–482 (1979).

Howell, C.R., and R.D. Stipanovic, "Suppression of *Pythium ultimum*–Induced Damping–Off of Cotton Seedlings by *Pseudomonas fluorescens* and its Antibiotic, Pyoluteorin," *Phytopathology*, 70:712–715 (1980).

Hutchins, A.S., "In Vitro Inhibition of Root–Rot Pathogens *Phellinus weirii, Armillariella mellea, Fomes annosus*, and *Phytophthora cinnamomi* by a Newly Isolated *Bacillus* sp.," *Microb. Ecol.*, 6:253–259 (1980).

Milner, J., et al, "Culture Conditions that Influence Accumulation of Zwittermicin A by *Bacillus cereus* UW85," *Appl. Microb. Biotech.*, (1995).

Misaghi, I.J., et al., "Fungistatic Activity of Water–Soluble Florescent Pigments of Fluorescent Pseudomonads," *Ecol. Epidem.*, 72:33–35 (1982).

Wakayama, S., et al., "Mycocerein, a Novel Antifungal Peptide Antibiotic Produced by *Bacillus cereus*," *Antimicrob. Agents. Chemother.*, 26:939–940 (1984).

*Primary Examiner*—Irene Marx
*Attorney, Agent, or Firm*—Quarles & Brady

[57] ABSTRACT

A novel strain of *Bacillus cereus*, designated DGA34, has been isolated from the environment. The strain DGA34 is one of a number of *B. cereus* strains which are useful as biocontrol agents to combat fungal damping off disease in field crop plants, in part because of their production of the antibiotic zwittermicin A. Strain DGA34 has exhibited the best performance among a large number of natural isolates in producing the highest titer of zwittermicin A production.

4 Claims, 1 Drawing Sheet

BACILLUS CEREUS STRAIN DGA34

TECHNICAL FIELD

The present invention is in the general field of bacteriology and relates, in particular, to a novel strain of bacteria useful as a source of the antibiotic zwittermicin A.

BACKGROUND OF INVENTION

Significant research has been conducted in recent years on the use of biological agents to increase agricultural productivity and efficiency. Biological control based on the use of microorganisms to suppress plant pests or supplement plant growth offers an attractive alternative to chemical pesticides which are less favored than they have previously been because of concerns about human health and environmental quality. Several screening programs have been used before to isolate biological agents which are effective in the laboratory or in the field to combat pests or facilitate plant growth.

An example of a biological control agent into which significant scientific and economic development has occurred is the use of the *Bacillus thuringiensis*. It was recognized that *B. thuringiensis* strains produced toxic proteins which have the ability to specifically kill certain insects and that initial inquiry led to a significant research which has proceeded to identify a large number of *B. thuringiensis* strains having variations and target range in efficacy. In addition, research has been conducted on methods for stabilizing and applying such toxins, or strains harboring them, to a wide variety of field crop situations. It was also discovered that knowledge of *B. thuringiensis* strains was largely transferable to new strains since the toxins required for biological control and methods for preparing inocula for use in the field were generally similar among strains.

Previously it has been found that a specific strain of *Bacillus cereus*, which has been referred to both as UW85 and by its ATCC designation 53522 has biocontrol efficacy in many applications. The UW85 *B. cereus* strain was found to protect alfalfa seedlings from damping off caused by *Phytophthora medicaginis*, tobacco seedlings from Phytophthora nicotianae, cucumber fruits from rot caused by *Pythium aphanidermatum*, and peanuts from *Sclerotinia minor*. UW85 is also described, by reference to its ATCC number in U.S. Pat. No. 4,877,738. It was later found that UW85 produced two antifungal compounds which contribute independently to its suppression of damping off fungi due to antifungal and antibacterial activity. The more potent of these compounds, a novel aminopolyol has been designated zwittermicin A while the second compound, not well characterized, has been provisionally designated antibiotic B.

"Biological control" is defined as pathogen suppression by the use of a second organism. Mechanisms of biological control are diverse. For example, certain enteric bacteria have been examined for their usefulness in biological control of root rot in alfalfa. It is believed that control is obtained by competition between the enteric bacteria and the fungi for space on the surface of the alfalfa roots. In contrast, a toxin produced by one species of bacteria may be used to control another species of bacteria that appears as a pathogen. Bacterially produced antibiotics are an example of such toxins. The toxin can be isolated from the species producing it and administered directly, as is the common procedure with penicillin, or the species itself may be administered under appropriate circumstances to produce the toxin in situ. Once identified, such toxins produced by soil-dwelling bacteria may have utility in diverse other areas as antifungal or antibiotic agents.

SUMMARY OF THE INVENTION

The present invention is summarized in that a novel *Bacillus cereus* strain, here designated DGA34, ATCC No. 55608, has been isolated from the environment, this strain having been found to have increased efficacy in the biosynthesis of the antifungal agent zwittermicin A.

The present invention is further characterized in that a method is described to create quantities of the biocontrol antibiotic zwittermicin A by the fermentation of a novel Bacillus cereus isolate designated DGA34, ATCC No. 55608.

Other objects, advantages, and features of the present invention will become apparent from the following specification.

DETAILED DESCRIPTION OF THE INVENTION

Figure 1:
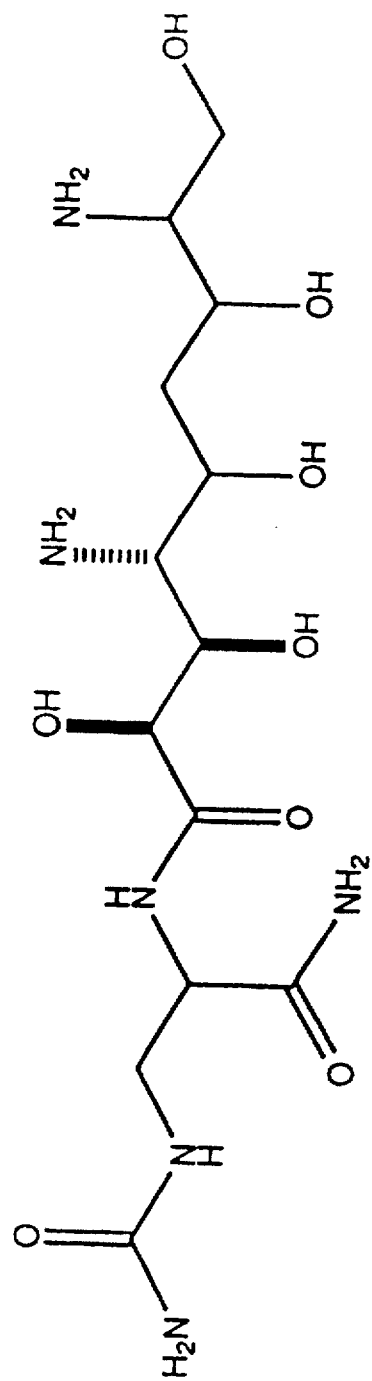
FIG. 1 shows the chemical structure of zwittermicin antibiotic.

An original bacterial strain, isolated from soil, exerts biological control over species of fungi responsible for damping off and root rot in plants. This strain has been designated by the present inventors, who isolated this strain, as *Bacillus cereus* strain DGA34. The strain has been deposited in the American Type Culture Collection, given the accession number ATCC 55608, and shall hereinafter be referred to either as Strain DGA34 or ATCC 55608. The *Bacillus cereus* strain 55608 has biocontrol characteristics similar to those of *B. cereus* strain 53522, also known as UW85, which is described in more detail in U.S. Pat. No. 4,877,738 which is hereby incorporated by reference.

These bacterial strains have been obtained in substantially pure cultures. A "substantially pure" culture shall be deemed a culture of a bacteria containing no other bacterial species in quantities sufficient to interfere with replication of the culture.

Strain DGA34 is one of a group of *Bacillus cereus* strains that have been identified as useful biocontrol agents due, at least in part, to the fact that they naturally synthesize antibiotic agents, notably an antibiotic which is the subject of a co-pending patent application. The antibiotic or toxin is found in supernatant fluid and other bacteria-free fluid and culture medium removed from a culture of DGA34 or of its protecting mutants. This toxin has been so characterized as to be identifiable independent of its source in cultures of *Bacillus cereus*, and is known and by the coined term "zwittermicin A." Another fraction from the supernatant fluid from a culture of *B. cereus* ATCC 53522 has been found biologically active, having a zoolysin capability to *Phytopthora medicaginis* (Pmm) zoospores, but, as revealed below, this zoolysin active fraction does not have the antifungal activity of the antibiotic. *Bacillus cereus* antibiotic zwittermicin A has been found to be a highly water soluble molecule of about 396 daltons. The molecule includes two amino groups, and is a poly-alcohol.

The zwittermicin A molecule has had its structure recently identified. Shown in FIG. 1 is the chemical structure of this novel zwittermicin antibiotic produced by several strains of *B. cereus*. the antibiotic has been found to be effective against a wide variety of fungal and bacterial microorganisms. Zwittermicin A also has utility as a fungal pathogen inhibitor itself. It is possible to apply zwittermicin A, purified from the bacillus which made it, to seeds or plants to successfully inhibit fungal disease.

The method by which the biological control referred to in the preceding paragraph may be verified to exist is the "plant protection assay" detailed below. "Biological control" of fungi causing damping off and root rot shall be deemed to exist if, when an effective quantity of DGA34, its mutants that exhibit biological control, the anti-fungal toxin produced by them, or any other compound or molecule is placed in the soil or other growing medium in the immediate vicinity of the plant to be protected, a statistically significant reduction in the symptoms of damping off or root rot occurs. An "effective quantity" to combat damping off and root rot shall be that quantity sufficient to result in such a visibly significant reduction of symptoms. Clearly, if no quantity of a bacteria or any toxin or other compound is an effective quantity as so defined, that bacteria, toxin, or compound is not capable of exerting biological control over the fungi causing damping off and root rot.

DGA34 and those of its mutants capable of exerting such biological control shall sometimes be referred to collectively as "protecting" bacteria. *Bacillus cereus* antibiotic and other toxins capable of exerting such biological control shall sometimes be referred to as "protecting" compounds or toxins. Plants, including seeds, seedlings, and mature plants, treated with such an effective quantity of protecting bacteria, their toxins, or *Bacillus cereus* antibiotic shall be referred to as "protected" from root rot or damping off.

The following is a disclosure of the plant protection assay whereby a test material such as a bacteria, a toxin, or the like, may be tested for its ability to exert biological control over a fungus capable of causing the symptoms of damping off or root rot. The seed or seedling of the plant to be protected is planted in a planting medium in the presence of damping off or root rot causing fungi. The planting medium may be a damp soil containing such fungi, vermiculite in water with the fungi present either in the vermiculite and water or in or on the seed or seedling, an agar-based formulation, or any other planting medium in which the seed or seedling will grow and the fungi may freely develop. The bacteria, toxin, or other test material is placed at least in the immediate vicinity of the seed or seedling. Such placement shall be understood to be in the "immediate vicinity" of the seed or seedling if any soluble test material or any soluble exudate of a bacteria being tested will be in actual contact with the germinating seedling.

Preferably, if seed is used, the seed is coated with the test material, and when the test material is so used with respect to a seed, it shall be referred to hereinafter as a "seed inoculum." The process of coating seed with a seed inoculum is generally well known to those skilled in the art, and any conventional method that does not require conditions sufficiently harsh to kill bacteria or destroy toxins or other materials included in the seed inoculum is adequate. An easy and preferred method is to suspend or dissolve the test material in a 1.5% aqueous solution of methyl cellulose. For convenience, it will be presumed hereinafter that the seed inoculum is a bacteria suspended in the methyl cellulose, although a dissolvable material such as a bacterial toxin may be handled in the same manner. The plant seed to be protected is added to the suspension and is mixed vigorously with it to coat the surface of the seed with the suspension. The seed may then be dried aseptically, preferably by being placed within a laminar flow hood on a sterile surface such as a sterile petri plate. The result is a dry, seed inoculum-coated seed. When the coated seed is planted in the planting medium, the test material accompanies it to reside in the immediate vicinity of the seed.

After a time sufficient for seedling growth and the expression of the symptoms of damping off, seedlings developing from the planted seed may be evaluated for visual evidence of protection, when compared to controls. In strains of alfalfa, soybeans, and snap beans known to be vulnerable to damping off, 2 weeks of growing time in a growth chamber at 24° C. with a 12 hour photoperiod was found to be a period sufficient for the expression of symptoms of damping off when seedlings were being grown in test tubes containing roughly $10^3$ zoospores of Pmm or comparable, damping off-causing fungi. Protected seeds developed into seedlings visually indistinguishable from uninfected seeds while control seedlings developing from unprotected seeds were killed or, in the case of snap beans, exhibited brown lesions on roots and stems, stunted roots, rotted roots, and other visually apparent symptoms of root rot.

As will become apparent below, many strains of *Bacillus cereus* are useful as biocontrol agents and produce the antibiotic zwittermicin A. Since application of purified zwittermicin A is contemplated, it is useful to quantitatively evaluate the levels of zwittermicin A produced by the various zwittermicin A-producing strains of *B. cereus*, this permits selection of high producing strains as candidates both for fermentation production of zwittermicin A as well as mutagenesis protocols to even further increase the production of zwittermicin A.

The procedure for quantitating the level of production of zwittermicin A is generally characterized as an end point dilution, and is described in detail in Silo-Suh, *Appl. Environ. Microbiol.*, 60:2023–2030 (1994). Briefly, dilutions of partially purified zwittermicin A samples and dilutions of predetermined amounts of zwittermicin A were subjected to high voltage electrophoresis. Zwittermicin A was detected by silver staining. The amount of antibiotic in the test sample was calculated by comparison of the end-point dilution at which zwittermicin A could be detected in the test sample as compared to the standard. The general limit of detection was 0.33 µg/ml. The level of zwittermicin A production was found to vary from sample to sample, but generally exceeded the amount of zwittermicin A produced by UW85.

Using this quantitative analysis of zwittermicin A production described above, several newly isolated strains were identified which had levels of zwittermicin A production greater than UW85, ATCC 53522. UW85 produced 19 micrograms of zwittermicin A per milliliter of culture media. By comparison the newly isolated strain DGA34 produced 56 µg/ml. DGA34 will generally produce, on average, in excess of 30 µg/ml. In a second replicate, DGA34 produced 35 µg/ml while UW85 produced 26.2 µg/ml.

The *B. cereus* strain DGA34, ATCC 55608, was isolated from a soil sample taken from a vineyard in Douglas Gully, Australia. Unlike many of the newly isolated *B. cereus* biocontrol strains, DGA34 can be distinguished from UW85 by colony morphology. On minimal media, DGA34 is a solid orange, as opposed to the sectored orange colonies produced by UW85. On rich media, after several days, the colonies of DGA34 are distinctly clearer, and less opaque, than similar colonies of UW85. In other ways, the strain resembles UW85, and it can be easily handled and grown in culture, thus strain DGA34 is the strain of choice for use in fermentation production of zwittermicin A and also becomes a suitable candidate strain for mutation to make other zwittermicin A producing mutants.

Zwittermicin A producing mutants of DGA34 include both naturally occurring and artificially induced mutants. For example, DGA34 is generally sensitive to the antibiotics rifampicin and neomycin. However, it is expected that naturally occurring mutants of DGA34 can be isolated that exhibited resistance to one or the other of these antibiotics. Certain of these mutants, as well as one naturally occurring mutant distinguishable from the parent DGA34 strain by the appearance of its colonies, will be found to produce even higher levels of zwittermicin A. Other mutants of DGA34 can be artificially induced by subjecting DGA34 to the mutagen N-methyl-nitrogoguanidine in conventional ways. Similar mutants have been made from other useful *B. cereus* strains, such as UW85 (ATCC 53522), as described in U.S. Pat. No. 4,877,738, the disclosure which is hereby incorporated by reference.

EXAMPLE 1

Origin of Strains

The geographic origins, and physical and chemical characteristics of the soil samples used in this study are listed in Table 1. All samples were taken from the surface horizon. Measurements of soil pH, organic matter, and the particle size were made by the University of Wisconsin Soil & Plant Analysis Laboratory (Madison, Wis.).

TABLE 1

Characteristics of soils used in this study

| Soil/Site | Country | pH | % Organic[a] | % Sand, Silt, Clay[b] | Most recent vegetation |
|---|---|---|---|---|---|
| Lutz | Panama | nd[c] | 5.5 | nd | Forest |
| Snyder-Molino | Panama | nd | 6.2 | nd | Forest |
| Barbour-Lathrop | Panama | nd | 7.1 | nd | Forest |
| Moroceli | Honduras | nd | 1.7 | nd | Maize-Beans |
| San Matias | Honduras | 5.8 | 1.5 | nd | Maize-Beans |
| LaVega1 | Honduras | 6.3 | 2.3 | nd | Beans |
| LaVega5 | Honduras | 5.9 | 2.5 | nd | Sorghum-Maize |
| Arlington WI | USA | 6.9 | 4.2 | 23, 68, 9 | Alfalfa |
| Hancock WI | USA | 6.6 | 0.8 | 87, 8, 5 | Alfalfa-Oats |
| Marshfield WI | USA | 6.5 | 3.1 | 23, 72, 5 | Alfalfa |
| Lancaster WI | USA | 7.1 | 2.3 | 19, 68, 13 | Alfalfa |
| Madison WI | USA | 7.0 | 3.2 | 27, 56, 17 | Alfalfa |
| Taos NM | USA | 8.1 | 4.3 | nd | Pasture |
| Tifton GA | USA | 6.3 | 1.0 | 87, 12, 1 | Tobacco |
| Douglas Gully | Australia | 6.1 | 2.2 | nd | Vineyard |
| Lelystad | Netherlands | 7.5 | 1.8 | 51, 36, 13 | Potatoes |

TABLE 2

Strains and isolates used in this study

| Strain(s)/Isolates | Origin |
|---|---|
| ATCC7064, ATCC27877, ATCC12826 | American Type Culture Collection |
| BGSC6A3, BGSC6E1, BGSC6E2, BGSC4A9, BGSC4B1, BGSC4C3, HD1, BGSC4E1, BGSC4F1, BGSC4G1, BGSC4H1, BGSC4I1, BGSC4J1, BGSC4S2 | Bacillus Genetic Stock Center |
| T | U. W. Bacteriology Dept. Collection |
| UW85 | Alfalfa root, Arlington, WI (26) |
| Soy130 | Soybean root, Walnut St. Farm, Madison, WI |
| ALF1, ALF9, ALF10, ALF13, ALF19, ALF23, ALF52, ALF53, ALF79, ALF83, ALF85, ALF94, ALF95, ALF98, ALF99, ALF108, ALF109, ALF115, ALF117, ALF133, ALF137, ALF144, ALF154, ALF157, ALF161, ALF166, ALF167, ALF173 | Roots of alfalfa plants planted in soil from Arlington, WI and grown in growth chamber |
| LUTZ21, LUTZ58, LUTZ128 | Lutz soil |
| SNY14, SNY42, SNY44, SNY45, SNY73 | Snyder-Molino soil |
| BAR78, BAR145, BAR177 | Barbour-Lathrop soil |
| MOR1, MOR28, MOR37 | Moroceli soil |
| SM32, SM43, SM44 | San Matias soil |
| VGA19, VGA118, VGA137 | LaVega1 soil |
| VGA562, VGA577, VGA598 | LaVega5 soil |
| AS7-4, AS8-4, AG8-13, AS4-12, ARL8 | Arlington soil |
| HS1-3, HS23-11, HS24-8, HS24-9 | Hancock soil |
| MS1-9, M53-2, M58-2 | Mansfield soil |
| LS2-2, LS2-12, LS33-2 | Lancaster soil |
| WS4-12, WS8-8, WS10-15, WS16-4, WS22-12 | Madison soil |
| TNM68, TNM155, TNM243 | Taos soil |
| TG38, TG42, TG126 | Tifton soil |
| DGA34, DGA37, DGA84, DGA94 | Douglas Gully soil |
| LN24, LN75, LN100 | Lelystad soil |

Based on the profiles of fatty acids from 47 isolates analyzed by five Star Labs (Branford, Conn.) and Microbial ID (Newark, Del.), all of the isolates were classified as members of the *B. cereus* group, which includes the species *B. mycoides*, *B. anthracis* and *B. thuringiensis*. The unique rhizoidal morphology of *B. mycoides* strains differentiates them from *B. cereus*, and none of the isolates in this collection display *B. mycoides*-like morphology. *B. anthracis* is not hemolytic and is usually sensitive to ampicillin and therefore was probably excluded from this collection. Differentiation between *B. cereus* and *B. thuringiensis* is difficult with standard methods. Therefore we have followed current recommendations and considered all isolates gathered in this study as *B. cereus*. Strains BGSC4A9, BGSC4B1, BGSC4C3, HD1, BGSC4E1, BGSC4F1, BGSC4G1, BGSC4H1, BTSC4I1, BGSC4J1 and BGSC4S2 were previously classified by others as *B. thuringiensis*, and that species designation was retained for those strains.

Assay for Sensitivity to Phage P7

The phages P7 (ATCC75237) and PB were used to help characterize the strains. The susceptibility of *B. cereus* strains to infection by phage P7 has proven to have a strong co-relation to biocontrol utility and antibiotic production. To propagate these phages, we spread a mixture of melted soft agar (4 g agar/1) with approximately $10^6$ PFU of phage and an excess of *B. cereus* strain UW85 on ½-strength TSA plates. Plates were incubated overnight at 28° C. and then the soft agar was scraped off the plates and suspended in ½-strength trypticase soy broth (½-strength TSB), (1 ml/plate). Agar and cells were removed by centrifugation, and the supernatant solution was passed through a 0.2 μm filter. Phage titers were typically $1\times10^{10}$ PFU/ml.

To screen large numbers of isolates for P7 sensitivity, grids of 48 isolates were grown on ¹⁄₁₀-strength TSA and then cells were transferred with a metal replicator onto ¹⁄₁₀-strength TSA plates that had been spread with dilutions of P7 such that they contained approximately $10^8$, $10^4$, and $10^3$ PFU/plate. A ¹⁄₁₀-strength TSA plate containing no phage was used as a control. Isolates that appeared to form patches with decreased growth or plaques on plates containing P7 were tested in the soft-agar overlay assay (described below) to determine if they were $P7^s$. Most isolates that were $P7^r$ in the primary screen were not re-tested.

In the second test for sensitivity of bacterial isolates to P7, each isolate was grown on ½-strength TSA and cells were scraped off plates and mixed in soft agar overlays to form lawns on fresh ½-strength TSA plates. Ten-fold dilutions of P7 were placed in 5-μl drops on the plates, which were then incubated at 28° C. If plaques appeared, the strain was designated P7-sensitive ($P7^s$). Lawns of two isolates, ARL8 and HS23-11, were cleared by undiluted drops of P7, but P7 did not form isolated plaques on these isolates at lower concentrations. The clearing due to high titer drops appeared to be due to P7 rather than a chemical present in UW85 lysates, since high titer drops of lysates of PB, which produces turbid plaques on UW85, did not cause clearing on lawns of ARL8 and HS23-11. Therefore these strains were also scored $P7^s$. Isolates whose lawns appeared unaffected by P7 were scored $P7^r$.

Assay for Inhibition of *Erwinia herbicola*

Inhibition of *E. herbicola* LS005 was assayed as described in Silo-Sub et al. *Appl. Environ. Microbiol.*, 60:2023–2030 (1994), with the following modifications. Three-day-old cultures of each *B. cereus* isolate grown in ½-strength TSB were tested to determine whether they inhibited *E. herbicola* on ¹⁄₁₀₀₀-strength TSA plates. Isolates that produced visible zones of inhibition of *E. herbocola* were tested again. Isolates that produced visible zones of inhibition in both tests were scored $Eh^+$. Isolates that did not noticeably inhibit *E. herbicola* in each of two initial tests were scored $Eh^-$. Some *B. cereus* isolates did not inhibit *E. herbicola* during initial testing but did after storage at −20° C., and certain isolates (ALF115,HD1 and BGSC4S2) had variable phenotypes producing either small zones of inhibition or no zone in subsequent tests; these were classified $Eh^-$.

Assay for Zwittermicin A and Antibiotic B

Zwittermicin A and antibiotic B were identified in culture supernatants by cation exchange chromatography using CM SEP-PAK cartridges (Millipore, Millford, Mass.) followed by high voltage paper electrophoresis (HVPE). The cation fraction from the equivalent of 4 ml of culture supernatant was applied to the paper, which was stained with silver nitrate after electrophoresis, described in Silo-Suh et al. supra. Isolates that produced material indistinguishable from either authentic zwittermicin A or authentic antibiotic B in HVPE were designated zwittermicin A producers or antibiotic B producers, respectively. To verify the structural identity of zwittermicin A produced by nine representatives of the collection of isolates, putative-zwittermicin A was purified from these isolates, and subjected to proton nuclear magnetic resonance spectroscopy ($^1H$—NMR) and fas atom bombardment mass spectrometry.

Assay for Suppression of Alfalfa Damping-Off

Bacterial isolates were grown for three days in ½-strength TSB and tested in an assay for damping-off. Each isolate was tested on fifteen plants in each of 7 separate experiments with the following exceptions: strain ATCC12826 was omitted from experiments 1 and 2; strain BAR78 was omitted from experiment 4; and strains WX8-8 and LS2-12 were omitted from experiment 5. Statistical analyses (analysis of variance, Dunnet's comparison test, standard error of least squared mean) were conducted using the SAS Computer Progra. The data from the seven experiments were pooled and analyzed as a single experiment with seven blocks.

Testing Diversity of Strains

To estimate the diversity of zwittermicin A and antibiotic B-producers, we sought to determine the minimum number of unique zwittermicin A and/or antibiotic B-producing strains in our collection. We considered isolates to be distinct strains only if phenotypic differences between them could be shown. Therefore, isolates were subjected to a series of phenotypic tests. All characterization was performed on isolates that had been colony purified on ½-strength TSA. To test for antibiotic resistance, isolates were streaked on ½-strength TSA containing tetracycline (5 μg/ml), neomycin (5 μg/ml), or chloramphenicol (1 μg/ml), and incubated at 28° C. overnight. Isolates that grew similarly when streaked in the presence or absence of antibiotic were classified as antibiotic resistant. to test isolates for pigment production, they were grown on MES minimal medium at 28° C. for seven days and then scored visually. MES minimal medium contained 9.76 g/L 2-[N-morpholine]ethan-sulfonic acid (MES), 2 g/L $(NH_4)_2SO_4$, 0.2 g/L $MgSO_4$.7 $H_2O$, 0.25 mg/L $MnSO_4$.7 $H_2O$, 1.25 g/L $K_2HPO_4$.3$H_2O$, 2 g/L L-glutamic acid, 10 mg/L thiamine, 15 g/L agar, 40 mg/L $FeCl_3$.6$H_2O$, 6 g/L sucrose and 1 mM of the amino acids threonine, serine, leucine, valine, and alanine, and was adjusted to pH 6.1. MES-Thr medium was MES minimal medium lacking threonine. We characterized the ability of isolates to grow on MES-Thr media by streaking isolates onto MES-Thr plates and incubating at 28° C. for four days and recording the rate of appearance of colonies for each strain. Phages ΦATCC 7064 and ΦATCC 27877 were obtained from the American Type Culture Collection and were propagated on bacterial strains ATCC 7064 and ATCC 27877, respectively. Phage Φ63 was propagated on strain Bt-1, and both Φ63 and Bt-1 were obtained from R. Landen. Sensitivity of isolates to phages Φ63, ΦATCC7064 and ΦATCC27877 was determined by the soft-agar overlay method described above for P7, with plaque formation as the indicator of sensitivity.

Association of Zwittermicin A Production with P7$^s$ and Eh$^+$ Isolates

It was known that *B. cereus* strain UW85 produces two antibiotics, the novel aminopolyol, zwittermicin A, and antibiotic B, that contribute to the suppression of alfalfa seedling damping-off. UW85 was originally identified in a labor-intensive screen for biological control activity. The study conducted above was intended to investigate whether sensitive to P7 (P7$^s$) and the ability to inhibit *E. herbicola* (Eh$^+$) were phenotypes that could be used to identify zwittermicin A producers and useful biocontrol strains.

4,307 *B. cereus* and *B. thuringiensis* isolates were screened for P7$^s$ and/or Eh$^+$ phenotypes. The isolates were obtained from geographically diverse soil samples collected at a total of 16 locations in five countries (Table 1 above), from alfalfa and soybean roots, and from stock culture collections (Table 2 above). the number of P7$^s$ or P7$^s$Eh$^+$ isolates identified from each source and the number of isolates tested were tabulated. P7$^s$ isolates were identified in samples from 14 of the 16 soils examined as well as from alfalfa and soybean roots. Of the 87 P7$^s$ isolates, all were Eh$^+$ except SNY73 and LN100. P7$^s$Eh$^+$ isolates were identified from each of the soils as well as from alfalfa roots. Among all the isolates tested, approximately 2% (85/4,307) of the isolates examined were P7$^s$Eh$^+$ and 7% (132/1,876) were P7$^r$Eh$^+$.

Quantitative Comparison of Zwittermicin A Production

This quantitative comparison was performed by the endpoint dilution analysis described above.

In a first study, the results were as set forth in Table 3 below.

TABLE 3

| Strain | | Zwittermicin A Production (μg/ml) |
|---|---|---|
| DGA34 | 5 reps | 56 |
| WS10-15 | 5 reps | 35 |
| UW85 | 5 reps | 19 |

A second study was conducted, with the results as set forth in Table 4 below.

TABLE 4

| Strain | | Zwittermicin A Production (μg/ml) |
|---|---|---|
| DGA35 | 7 reps | 35 |
| UW85 | 6 reps | 26 |

What is claimed is:

1. A biologically pure culture of *Bacillus cereus* having all of the identifying characteristics of *B. cereus* strain DGA34, ATCC 55608.

2. A biologically pure culture of a mutant strain obtained from a culture having all of the identifying characteristics of *Bacillus cereus* strain DGA34, ATCC 55608, the mutant strain having the ability to produce zwittermicin A in excess of 50 μg/ml.

3. An inoculum for application to alfalfa comprising a carrier and an effective quantity of bacteria selected from the group consisting of *Bacillus cereus* DGA34, ATCC 55608, and mutants of *Bacillus cereus* DGA34, ATCC 55608, which produce zwittermicin A in excess of 50 μg/ml.

4. A method for producing zwittermicin A comprising culturing in a suitable medium an effective quantity of bacteria selected from the group consisting of *Bacillus cereus* DGA34, ATCC 55608 and mutants thereof which produce zwittermicin A, and recovering the zwittermicin A produced.

* * * * *

UNITED STATES PATENT AND TRADEMARK OFFICE
CERTIFICATE OF CORRECTION

PATENT NO. : 5,736,382
DATED : April 7, 1998
INVENTOR(S) : Jo Handelsman; Lynn M. Jacobson; Eric V. Stabb It is certified that error appears in the above-indentified patent and that said Letters Patent is hereby corrected as shown below:

Column 1, line 2:

--This invention was made with United States government support awarded by the following agencies: USDA Grant# 92-34190-6941. The United States has certain rights in this invention.--

Signed and Sealed this

Seventh Day of July, 1998

Attest:

BRUCE LEHMAN

*Attesting Officer*     *Commissioner of Patents and Trademarks*